United States Patent [19]

Hickmann et al.

[11] 4,028,445

[45] June 7, 1977

[54] APPARATUS FOR WETTING RESPIRATORY GAS

[75] Inventors: Karl Hickmann; Dieter Sahmkow, both of Lubeck, Germany

[73] Assignee: Dragerwerk Aktiengesellschaft, Germany

[22] Filed: Apr. 14, 1976

[21] Appl. No.: 676,648

[30] Foreign Application Priority Data

Apr. 15, 1976 Germany ............................ 2516496

[52] U.S. Cl. ............................. 261/142; 128/173.2; 128/192; 219/275; 219/302; 222/146 HE; 239/136; 261/DIG. 65
[51] Int. Cl.² .......................................... A61M 15/00
[58] Field of Search ..................... 261/DIG. 65, 142; 128/186, 192, 193, 212, 173.2; 219/271, 272, 273, 275, 302; 239/136; 222/146 HE

[56] References Cited

UNITED STATES PATENTS

| 2,755,372 | 7/1956 | Fisher, Sr. et al. | 219/275 |
| 2,763,765 | 9/1956 | Duberstein et al. | 219/275 |
| 3,579,263 | 5/1971 | Corbett et al. | 128/192 |
| 3,916,891 | 11/1975 | Freytag et al. | 261/142 |
| 3,971,913 | 7/1976 | Myklebust | 261/142 |

*Primary Examiner*—Tim R. Miles
*Assistant Examiner*—Gregory N. Clements

*Attorney, Agent, or Firm*—McGlew and Tuttle

[57] ABSTRACT

An apparatus for wetting respiratory gas comprises a receiver having an interior wetting chamber and a cartridge receiving chamber which communicates at its lower end with the wetting chamber and which has an open end for receiving a heater cartridge. The heater cartridge is disposable in the cartridge receiving chamber and it includes an inner portion containing a heater element and an outer sleeve portion which has a lower end disposed in the wetting chamber and has side walls which are spaced from the wall of the inner portion of the cartridge containing the heater element. The receiver contains a duct for supplying water into the space between the sleeve and the inner portion of the cartridge containing the heater so that the water will be heated in its passage around the inner portion and may be discharged through openings at the lower end of the sleeve into the wetting chamber. The receiver also contains a duct for respiratory gas which is directed into an annular space between the sleeve and the walls bounding the cartridge receiving chamber for flow downwardly over the wetting chamber and out through a nozzle discharge after it has picked up a quantity of moisture. Air which is exhaled from a patient is directed through the receiver in a location adjacent the wetting chamber.

4 Claims, 2 Drawing Figures

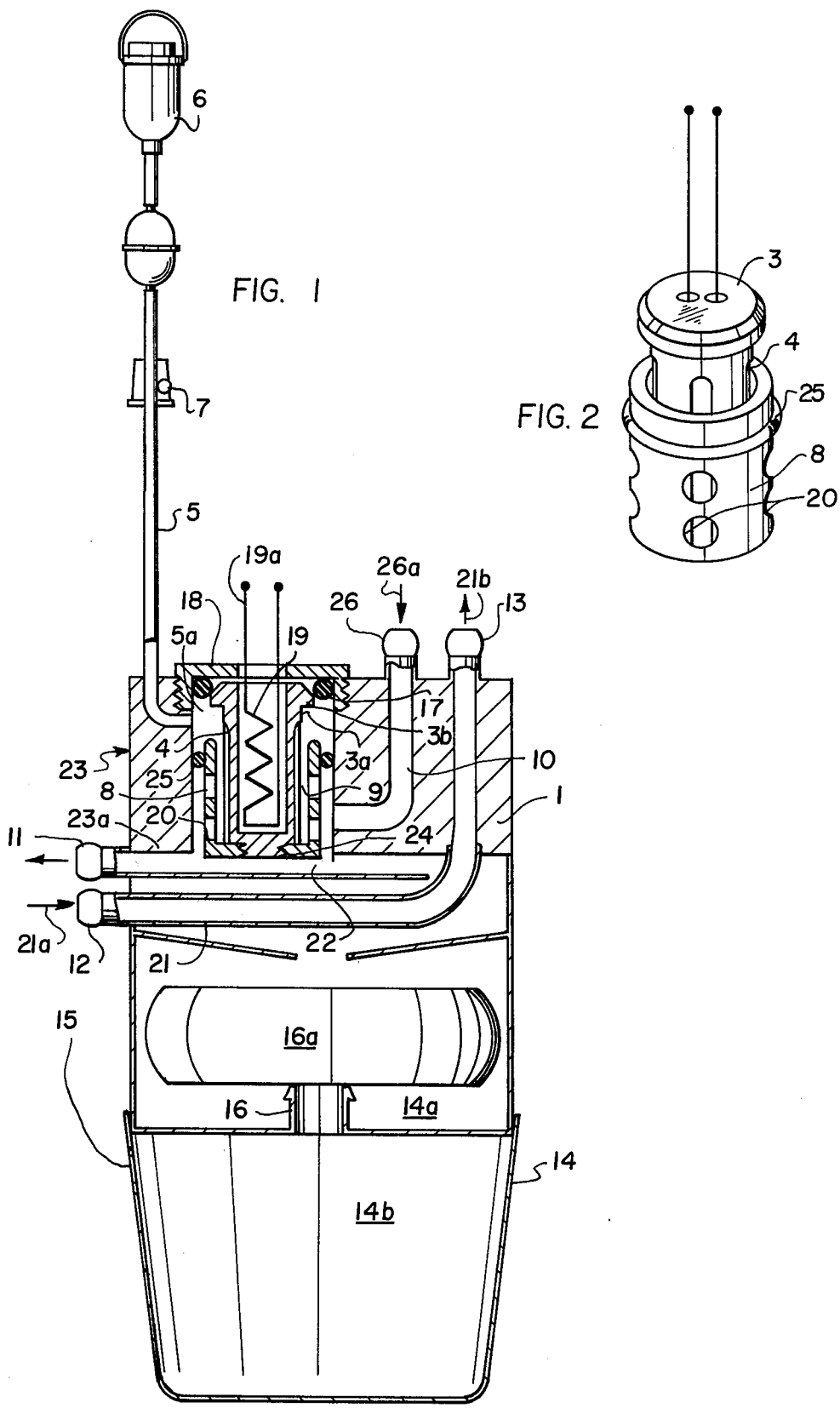

APPARATUS FOR WETTING RESPIRATORY GAS

BACKGROUND OF THE INVENTION

1. FIELD OF THE INVENTION

This invention relates in general to devices for adding moisture to gases which are delivered to a patient for breathing and in particular to a new and useful device for wetting respiratory gases.

2. DESCRIPTION OF THE PRIOR ART

When exhaling a patient loses water in each exhaling phase due to the wetting of the air in its passage through the lungs. Care must therefore be taken when respirating a patient that water is supplied to the respiratory gas in each respiration phase in order to compensate for the water lost.

An atomizer is known for supplying liquid particles into a main gas current conducted to the patient and in such a construction an atomizer nozzle is surrounded by a jacket. In order to shield the liquid particles from the main gas current, its bottom end protrudes into the main gas current below a point at which the liquid impinges on the impact surface to divide the liquid particles. The liquid particles are distributed with the atomizer air current inside the jacket. The larger liquid particles which are undesired for therapy then drift down while the small liquid particles enter the main gas current and are fed to the patient. This arrangement is elaborate in its design and is used for supplying atomized medicine for long term therapy. A disadvantage of the known device is that the respiratory air cannot be heated. As far as wetting takes place it is not controllable. The sterilization of the apparatus also presents difficulties.

A known apparatus for wetting and heating air which is to be inhaled by an artificially respirated patient, consists of a tank for the water to be coverted to steam at a desired temperature. The tank is heated from the outside. It can be removed from the heating system for sterilization. The tank has a cover which provides an air space above the water level. Conducting means transfer the heat to the evaporation surfaces in the air space above the water level. The steam in the air space is absorbed by the respiratory air flowing through the air space and it is fed to the patient. Heat control means control the temperature and the moisture content. Another heater in a part of the wetting apparatus forming a tube is so designed that the temperature rise in the respiratory air in this part of the arrangement is equal to or greater than the temperature drop of the air thus heated on its way between the outlet of this heater and the patient. The maximum desired temperature is not exceeded. The object of this additional heater which complicates the arrangement is to avoid the formation of condensate. The engineering effort of the entire system is quite considerable. The total amount of water must be heated. Special regulation and control means are required. Furthermore, it is disadvantageous that the sensitive electrical parts of the apparatus must be disconnected before it can be stabilized with any degree of reliability. The great air space in the tank makes it difficult to maintain a constant volume of the respiratory air to be conducted therethrough.

Another known gas wetting apparatus for a respirator contains a water evaporation chamber for evaporating water at a water level. The water to be evaporated is supplied through a water filling connection with a float seal. The float seal can also be provided in a separate float chamber. The two chambers the evaporation chamber and the float chamber, are then connected with each other through a water conduit. The pressure between the gas compartments of the two chambers is equalized by a gas connection in the form of an opening or pipe having a small cross section. In order to insure the evaporation of the water on the surface in the evaporation chamber, a heating element is arranged in the water of the evaporation chamber. The flow chamber has an overflow duct closed by a float actuated valve so as to prevent a rise in the water level when the float seal on the water filling connection does not work properly due for example to a calcuim deposit, fouling, etc. In this complicated gas wetting apparatus the gas to be wetted is enriched with water above a water surface. In order to obtain a sufficient amount of steam, the evaporation surface and hence the entire water evaporation chamber must be large. The evaporation also depends to a great extent on the temperature of the water and on the velocity of the streaming gas as well as the resulting cooling of the water surface. An exact control is therefore very complicated unless exact dosing is not necessary. The sterilization of the evaporation chamber must either by effected together with the flow chamber and the float seal in the overflow valve or the gas wetting apparatus must first be disassembled.

Another known apparatus for wetting the respiratory air with a collecting vessel for the condensate contains an evaporated insert in the housing that is traversed both by the respiratory air and the exhaling air. This evaporator insert has a heating element. It is traversed by a water conduit into which the water to be evaporated is introduced. Below the housing is connected a collecting vessel into which the evaporated water or the condensate is introduced either through a nozzle or through a float valve. The mixing of the steam issuing from the water conduit with the respiratory air is effected in the clearance space of the housing where the respiratory air is introduced. The air leaves again to flow in the air feeding system to the patient after it has been heated by the heating element and has mixed with the steam issuing from the water conduit.

The regulation of the water supply to the evaporated must be very sensitive because only steam is to escape from the water conduit. But if the heating temperature is too high, deflagrations will occur so that the water and the steam are ejected. The clearance space of the housing is relatively large due to the respiratory air which flows through the housing. Outside of the evaporator insert over which both the respiratory air and the exhaling air must pass, the temperature is low in the clearance space, as is proper for heating the respiratory air, but this also tends to enhance the growth of bacteria. The necessary disinfection of the device is not simple and can only be done after completely disassembling the apparatus.

SUMMARY OF THE INVENTION

In accordance with the present invention an apparatus for wetting the respiratory gases of patients is provided which is simple in design and simple to regulate and to sterilize. The wetting chamber in which the steam is mixed with the respiratory gas should be small so that it contains only a small respiratory gas volume. The wetting chamber should not become a source of a possible contamination of the respiratory gas and germs.

According to the invention the evaporator comprises a boiling cartridge or heated cartridge which is provided with an electrical heating element and with evaporation channels through which water to be evaporated must pass. The cartridge includes an inner chamber in which a heating element is positioned and which is surrounded by sleeves which are spaced from the heating chamber and from the interior walls of the receiver housing for the cartridge. The sleeve is provided with escape holes for the passage of water to be evaporated which is introduced at the top of the sleeve in the space between the sleeve and the inner housing containing the heater. The annular space for the passage of water permits the boiling of the water in such area and the escape of water and vapor down into a wetting chamber below the sleeve. The lower end of the sleeve protrudes into the wetting chamber.

A particular advantage of the invention is that the water to be evaporated is fed to the hot boiling cartridge over the torus or annular passage space for flow through a very short path and it is kept in the water duct sleeve close to the surface of the high temperature central heater cartridge portion. This results in a spontaneous evaporation of the water and steam is produced which is conducted through escape holes in the sleeve directly into the wetting chamber at which moisture collects. Furthermore it is of great advantage that the respiratory gas is heated by the close flow around the sleeve to such an extent that condensation during the further flow of the respiratory gas is avoided. The high temperature of the boiling cartridge close to the boiling point prevents effectively the growth of any bacteria. This is extremely important for low-germ treatment of the patient.

In accordance with one embodiment of the invention the water duct sleeve is screwed onto the central heater cartridge or boiling cartridge. The steam holes in the sleeve have a diameter which is greater than the distance between longitudinally extending and peripherally spaced channels which are defined around the heater cartridge inner portion. This embodiment also permits a simple design which is necessary for easy disassembly and reassembly of the apparatus because only this insures that the necessary cleaning and disinfection can actually be carried out by the personnel. The large steam escape holes make a preferential location of the water duct sleeve on the boiling cartridge unnecessary. In a particularly advantageous design the water duct sleeve has a circumferential packing to seal it into the receiver so that the upper portion of the sleeve which communicates with the water supply seal from the lower portion which has the openings for the discharge of the heated vapors into the wetting chamber. The circumferential packing by which the annular water duct surrounding the central heating element is separated from the sleeve is constructed in a simple manner from the duct for the respiratory air and the wetting chamber in which the steam is mixed homogeneously with the respiratory gas. The construction permits the installation of the evaporator without any preferential positioning thereof. This enhances the easy handling during cleaning and disinfection.

Accordingly it is an object of the invention to provide an improved apparatus for wetting respiratory gas which includes a receiver having an interior wetting chamber and a cartridge receiving chamber with the lower end communicating with the wetting chamber and opening at the top for receiving a cartridge which is positioned therein and which includes a central heater portion containing a heating element and a sleeve portion surrounding the central heating portion which is spaced from the walls of the housing walls bounding the receiving chamber and which communicates at its lower end with the wetting chamber and is provided with openings through the wall for the passage of vapors if the water is admitted to the space between the sleeve and the inner heater at the location of the upper end of the sleeve.

A further object of the invention is to provide an apparatus for wetting respiratory gas which is simple in design, rugged in construction and economical to manufacture.

For an understanding of the principles of the invention, reference is made to the following description of a typical embodiment thereof as illustrated in the accompanying drawings.

BRIEF DESCRIPTION OF THE DRAWINGS

In the Drawings:

FIG. 1 is a partial longitudinal sectional view and elevational view of an apparatus for wetting respiratory gases constructed in accordance with the invention; and FIG. 2 is a front top perspective view of a heater cartridge employed with the device of FIG. 1.

GENERAL DESCRIPTION OF THE PREFERRED EMBODIMENT

Referring to the drawings in particular the invention embodied therein comprises a receiver generally designated 23 which includes a housing 1 which has an interior wetting chamber 22 which is in communication with the lower end of a cartridge receiving chamber 23a.

In accordance with the invention a heater or boiler cartridge generally designated 3 is positioned into the cartridge receiving chamber 23 and it includes a cover fastening portion 18 which is threaded into a threaded upper portion of the chamber 23a. The cartridge 3 includes a central heater portion or heater cylinder 3a containing a heater element 19 which may be electrically connected through the terminals 19a to provide a resistance heating of the central portion 3a. To facilitate heat transfer the central portion 3a comprises a cylinder having a periphery with longitudinally extending and circumferentially spaced recesses 4. An annular evaporation space 9 is defined between the central portion 3a and an outer sleeve 8 which has walls spaced from the periphery of the central portion 3a and an outer surface which is spaced inwardly from the walls bounding the cartridge receiving recess 23a.

The receiver 23 includes a water duct connection 5 leading into a water inlet space 5a which is sealed at the upper end by an annular packing 17 and at the lower end by an annular packing 25. The water to be evaporated passes through the space 5a into a space between the top of the sleeve 8 and an upper portion 3b of the heater cartridge 3. The sleeve 8 and the central portion 3a of the cartridge 3 are advantageously interconnected by threaded connection 24.

In accordance with a feature of the invention the sleeve 8 is provided with steam escape holes 20 having diameters which are greater than the spacing between the evaporation channels 4. A respiratory gas duct 10 is also defined in the receiver 23 and it has a nozzle inlet 26 for the inflow of respiratory gas in the direction of the arrow 26a. The respiratory gas flows into an annular space between the exterior walls of the sleeve 8 and the interior walls bounding the cartridge receiving chamber 23a and thence downwardly into the wetting chamber 22. The respiratory gas is then fed to the patient through a nozzle 11 connected in the respiratory supply system.

Air which is exhaled from the patient is directed in the direction of arrow 21a through a nozzle 12 and through a passage 21 and discharged out through a nozzle 13 in the direction of arrow 21b.

The lower portion of the wetting chamber 22 is connected with a collecting vessel 14. The connection is effected through a float valve 16 which opens when water is collected in an intermediate chamber portion 14a to cause a float 16a to move off a float valve seat 16 and permit communication between the intermediate chamber 14a and the chamber 14b of the collecting vessel 14. The pressure is equalized in a chamber 14b by an opening 15.

The water required for wetting the respiratory gas is introduced into the duct 5 from a water supply 6 under the control of a clamp 7. The water flows through the entrance 5a and into the annular space 9 and it immediately evaporates while flowing around the central portion 3a. The steam then enters the respiratory gas feed line through the steam escape holes 20 and finally mixes with the respiratory gas in the wetting chamber 22.

While a specific embodiment of the invention has been shown and described in detail to illustrate the application of the principles of the invention, it will be understood that the invention may be embodied otherwise without departing from such principles.

What is claimed is:

1. An apparatus for wetting respiratory gas, comprising a receiver having an interior wetting chamber and a cartridge receiving chamber with one end of said cartridge receiving chamber communicating with the wetting chamber and having an opposite end defining a cartridge receiving chamber opening, a water supply duct connected into the cartridge receiving chamber, a respiratory gas connected into the cartridge receiving chamber, and a heater cartridge in said cartridge receiving chamber comprising an inner portion, heater means in said inner portion for boiling water to evaporate it, a sleeve surrounding said inner portion and defining an annular water heating space therebetween having an opening for the passage of water into the wetting chamber, said sleeve being spaced from said inner portion and from the walls of the housing bounding said cartridge receiving chamber and having a lower closed end disposed in said wetting chamber, said water supply ducts being located to direct water into the annular water heating space defined between said sleeve and said inner portion.

2. An apparatus according to claim 1, wherein said sleeve has a closed bottom threaded to said inner portion, said inner portion comprising a cylinder having longitudinally elongated and circumferentially spaced recesses defined on its periphery, there being a plurality of openings in said sleeve each having a diameter which is greater than the spacing between said recesses.

3. An apparatus according to claim 1, including an annular packing disposed between said sleeve and the walls of said housing and sealing the top of said sleeve with said housing from the bottom thereof.

4. An apparatus according to claim 1, wherein said cartridge comprises an inner cylinder, a cover for said cartridge threaded into said receiver at the location of the cartridge receiving opening and supporting said cartridge in the cartridge receiving chamber, a first sealing ring disposed between said sleeve and the walls surrounding the cartridge receiving chamber and a second sealing ring above said first sealing ring between said inner portion of said heater cartridge and said cover interior, said water conduit being connected into said receiver and discharging into the space between said first and second seals, said sleeve being separated from an upper portion of said inner part of said heater cartridge so as to define an inflow for the water into the annular space between said sleeve and said inner portion.

* * * * *